(12) United States Patent
Fajt et al.

(10) Patent No.: US 8,067,047 B2
(45) Date of Patent: Nov. 29, 2011

(54) METHOD AND DEVICES FOR FORMING ARTICLES

(76) Inventors: James Fajt, College Station, TX (US); Bruce Dorendorf, Winnebago, MN (US)

( * ) Notice: Subject to any disclaimer, the term of this patent is extended or adjusted under 35 U.S.C. 154(b) by 950 days.

(21) Appl. No.: 11/768,446

(22) Filed: Jun. 26, 2007

(65) Prior Publication Data

US 2007/0298082 A1    Dec. 27, 2007

Related U.S. Application Data

(60) Provisional application No. 60/805,930, filed on Jun. 27, 2006, provisional application No. 60/824,688, filed on Sep. 6, 2006.

(51) Int. Cl.
*A23K 3/00* (2006.01)
*A23L 1/00* (2006.01)
*A23L 1/05* (2006.01)

(52) U.S. Cl. .......... 426/285; 426/54; 426/512; 426/516; 426/573

(58) Field of Classification Search .............. 426/53, 426/54, 573, 575, 512, 516, 285
See application file for complete search history.

(56) References Cited

U.S. PATENT DOCUMENTS

| | | | |
|---|---|---|---|
| 3,862,336 A | 1/1975 | Kofsky et al. | |
| 3,889,007 A | 6/1975 | Gunter et al. | |
| 4,030,328 A * | 6/1977 | Wagner et al. | 72/45 |
| 4,153,735 A * | 5/1979 | Mommer | 426/285 |
| 4,272,234 A | 6/1981 | Tse | |
| 4,733,971 A | 3/1988 | Pratt | |
| 4,815,042 A | 3/1989 | Pratt | |
| 4,844,936 A | 7/1989 | Cox et al. | |
| 4,889,433 A | 12/1989 | Pratt | |
| 4,910,024 A | 3/1990 | Pratt | |
| 4,921,108 A | 5/1990 | Berta | |
| 4,935,250 A | 6/1990 | Cox | |
| 5,219,224 A | 6/1993 | Pratt | |
| 5,306,478 A | 4/1994 | Hayati et al. | |
| 5,314,537 A | 5/1994 | Berta | |
| 5,340,211 A | 8/1994 | Pratt | |
| RE34,776 E | 11/1994 | Pratt | |
| 5,369,032 A | 11/1994 | Pratt | |
| 5,401,501 A | 3/1995 | Pratt | |
| 5,431,927 A * | 7/1995 | Hand et al. | 426/2 |
| 5,520,942 A | 5/1996 | Sauer, Jr. et al. | |
| 5,525,353 A | 6/1996 | Fajt | |
| 5,674,518 A | 10/1997 | Fajt | |

(Continued)

OTHER PUBLICATIONS

Akdogan, Hulya, "High Mousture Food Extrusion," International Journal of Food Science and Technology 1999, 34, 195-207.

(Continued)

*Primary Examiner* — Lien T. Tran
*Assistant Examiner* — Katherine Deguire
(74) *Attorney, Agent, or Firm* — McPherson IP Law Office, PLLC

(57) ABSTRACT

The present invention is predicated upon methods and devices for forming numerous articles for various applications including nutritional applications, medicinal applications, or other useful applications for plants, animals or otherwise. In one aspect, the present invention provides methods and devices for forming high quality pellets using alginates as a retention agent for the ingredients. This may be achieved through the creation or modification of pre-existing forming devices, wherein an alginate applicator is provided for applying the alginate to the ingredients, before, during or after formation of the articles, or combinations thereof, to retain the ingredients of the articles together.

19 Claims, 2 Drawing Sheets

U.S. PATENT DOCUMENTS

| | | | |
|---|---|---|---|
| 5,767,107 | A | 6/1998 | Chaundy et al. |
| 5,853,244 | A | 12/1998 | Hoff et al. |
| 6,156,120 | A | 12/2000 | Heffels et al. |
| 6,238,727 | B1 | 5/2001 | Takemoto et al. |
| 6,399,117 | B1 | 6/2002 | Hoff et al. |
| 6,403,142 | B1 | 6/2002 | McDaniel, III et al. |
| 6,423,346 | B1 | 7/2002 | Hansen et al. |
| 6,528,100 | B1 | 3/2003 | Hoff et al. |
| 6,623,776 | B1 | 9/2003 | Wathne et al. |
| 6,783,792 | B2 | 8/2004 | McDaniel, III et al. |
| 6,793,937 | B2 | 9/2004 | Quong |
| 6,800,306 | B1 | 10/2004 | Baekken et al. |
| 6,830,771 | B2 | 12/2004 | Lanter et al. |
| 6,921,458 | B2 | 7/2005 | Chickering, III et al. |
| 7,069,876 | B2 | 7/2006 | Harris, Jr. et al. |
| 7,240,807 | B2 | 7/2007 | Hoff et al. |
| 7,325,967 | B2 | 2/2008 | Hoff et al. |
| 7,396,548 | B2 | 7/2008 | Kyle |
| 7,410,078 | B2 | 8/2008 | Hoff et al. |
| 7,537,375 | B2 | 5/2009 | Hoff et al. |
| 2006/0060602 | A1* | 3/2006 | Jeong .................... 222/52 |
| 2008/0312345 | A1 | 12/2008 | Rajsharad et al. |
| 2010/0075019 | A1 | 3/2010 | Scheer |

OTHER PUBLICATIONS

Ristow et al, "Effects of Dietary Fiber on the Bioavailability of Folic Acid Monoglutamate," Journal of Nutrition, vol. 112, Issue 4, 1982, p. 750-58.

Corrier et al., "Competitive exclusions of *Salmonella enteritidis* in Leghorn chicks" comparison of treatment by crop gavage drinking water, spray, or lyophilized alginate beads, Avain diseases, vol. 38, Issue 2, 1994 p. 297-303.

Colvin et al., "Effects of Sodium alginate on absorption and deposition of radioactive cations in the chick." Proceedings of the Society for Experimental Biology and Medicine, vol. 124, Isssue 2, 1967, p. 566-68.

Cool Feed Press Release, "Aquacenter's new 'Cool Feed Process' creates medicated pellets that float." (available at http://www.tecinfo.com/~aquacenter?coolfeed.html, last accessed Sep. 1, 2006).

MSU Cares, "A practical Guide to Nutrition, Feeds, and Feeding of Catfish," Bulletin 1041—Mar. 1996 (available at http://msucares.com/[ubs/bulletins/b1041.htm, last accessed Aug. 4, 2006).

Hasting et al., "Aquaculture development and coordination programme, Fish Feed technology." Chapter 18. Feed Milling Process (available at http://www.fao.org/docrep/X5738E/x5738e0j.htm, last accessed Aug. 4, 2006).

"A guide to the Seaweed Industry . . . ," Chapter 5. Alginate (available at http://www.fao.org/DOCREP/006/Y4765E/y4765e08.htm, last accessed Sep. 1, 2006).

Wikipedia, "Alginic Acid," (available at http://en.wikipedia.org/wiki/Alginic_acid, last accessed May 24, 2007).

Wikipedia, "Sodium alginate," (available at http://en.wikipedia.org/wiki/Sodium_alginate, last accessed May 24, 2007).

http://www.andritz.com/sm_26v400wn.jpg, last accessed Aug. 17, 2006.

http://www.andritzsproutbauer.com/images/bio-pellet-mill-26LM.jpg, last accessed Jul. 17, 2006.

http://img.alibaba.com/photo/50167478/Pellet_Mill_For_Poultry_And_Fish_Products.jpg, Last accessed Aug. 17, 2006.

http://www.andritz.com/pm30.jpg, last accessed Aug. 17, 2006.

http://img.alibaba.com/photo/50669014/Pellet_Mill_SZLH350_.jpg, last accessed Aug. 17, 2006.

http://www.agrimill.com/images/productimages/39.jpg, last accessed Aug. 17, 2006.

http://env.kubota.co.jp/01recycle/gm/images/pellet_mill/pellet_figure.jpg, last accessed Aug. 17, 2006.

http://www.russelplastics.co.uk/images/extruder.gif, last accessed Aug. 17, 2006.

http://www.mischer.com/grundlagen /artikel/blider/extruder-1.gif, last accessed Aug. 17, 2006.

http://www.gealan.de/media/extruder.gif, last accessed Aug. 17, 2006.

http://www.troester-usa.com/WIRE?EPH-extruder.gif, last accessed Aug. 17, 2006.

http://www.strictly-extrusion.com/maintenance/main.htm, last accessed Aug. 17, 2006.

http://www.americankuhne.com/images/Extruder.gif, last accessed Aug. 17, 2006.

http://www.allproducts.com/manuracture97/rubbermix/product4jpg, last accessed Aug. 17, 2006.

\* cited by examiner

METHOD AND DEVICES FOR FORMING ARTICLES

CLAIM OF PRIORITY

This application claims the benefit of the filing dates of U.S. Provisional Application Nos. 60/805,930, filed Jun. 27, 2006, and 60/824,688, filed Sep. 6, 2006, the contents of which are hereby entirely incorporated by reference for all purposes.

FIELD OF THE INVENTION

The present invention is predicated upon methods and devices for producing customized consumable articles for various applications including animals, plants or otherwise.

BACKGROUND OF THE INVENTION

The formation and use of consumable (e.g. absorbable) articles with plants, animals, or otherwise has been done in the past for providing nutrition, medication and other benefits. The ingredients of these articles may vary to correspond to the needs of the recipient. With the demand for consumable articles being so high, mass producing devices are often used. Such forming devices may comprise extruding devices, pellet mills, or the like, wherein large amounts of individual articles are formed in a relatively short period of time. However, in lower production applications it is also contemplated that other forming devices may be used as well.

Prior methods of forming articles, particularly pellet like articles, utilize starch for retention of the ingredients. The use of starch requires heat and pressure for retention of the ingredients. This is due to the fact that starch requires the use of heat and pressure to unravel the molecular strands of the starch and re-attaching the strands to each other or other ingredients of the articles.

Unfortunately, the use of heat for retention of the ingredients not only prolongs the time period for forming articles, but also uses unnecessary energy. Furthermore, the application of heat, at times, is destructive to some of the ingredients of the articles such as with certain medication, enzymes, vaccines, and growth promoters or otherwise. Accordingly, the use of heat increase production cost and limits the ability to form customized articles.

In another aspect, the use of starch as a retention agent has proven to be less than perfect, particularly as a retention ingredient of pellet articles, or the like. It has been found that using starch as a retention agent fails to maintain the integrity of the articles to a desired level. For example, with the use of starch as a retention agent there is expected a certain percentage of fines (e.g. article fragments) that are unusable. In view of these and other deficiencies in the use of starch as a retention agent, particularly with pellet articles, there is a need for a new retention agent for maintaining the ingredients of articles together without the necessary use of heat and pressure. Furthermore, there is a need for a new retention agent which results in reduced fines, smoother surfaces (e.g. less bridging) and moisture and/or water stability.

SUMMARY OF THE INVENTION

The present invention improves on the prior art by providing methods and devices for forming high quality articles, particularly pellets or the like. In one aspect, this improvement is in the form of a new retention agent adapted to be added and/or mixed with the ingredients forming the articles to limit and/or control separation after forming thereof. In a preferred configuration, the retention agent of the present invention comprises an alginate, such as sodium alginate or otherwise.

One advantage of the present invention is that the retention agent may be substantially free of starch for retaining the ingredients. The absence of starch as a retention agent, and limitations thereof, allows for a greater range of available ingredient configurations for the articles. Not only is starch no longer required as an ingredient, but ingredients previously thought to be difficult to maintain together (such as fats or otherwise) can be highly concentrated within the ingredients of the articles. Also, this absence also reduces manufacturing cost as the amount of heat and/or pressure required may be reduced or even eliminated as the retention agent is configured for use at ambient or elevated temperatures and pressure ranges.

The present invention also provides improved methods and devices for forming the articles, through the use of alginates as a retention agent. As described herein, the articles may be configured for numerous applications. For example, the articles may be configured for different types of recipients and/or for different purposes (e.g. nutritional, medicinal or otherwise), as described herein.

In one aspect, the present invention provides a method of forming a pellet for feed. The method includes the steps of combining one or more ingredients to form a first mixture, wherein the first mixture includes at least one dietary ingredient selected from fats, carbohydrates, proteins, or combinations thereof. The method also includes the steps of combining one or more ingredients to form a second mixture, wherein the second mixture includes an alginate. The first mixture is formed into a plurality of pellets through a forming device, wherein before, during or after forming of the articles the second mixture is added to the first mixture, and wherein the second mixture retains the ingredients of the first mixture together.

In another aspect, the present invention provides a food pellet article. The article includes a retention agent including water and 0.1% to 10% by weight sodium alginate. The article furthering includes an ingestible food mixture including ingredients selected from carbohydrates, protein, fat or combinations thereof, wherein the ingestible food mixture is formed into a pellet and wherein the retention agent maintains the ingredients together without the use of starches.

In still another aspect, the present invention provides a method of formulating articles of food. The method includes the steps of: i) providing a forming device adapted for forming a plurality of articles through a die, the forming device including a first storage container for holding ingredients to be formed by the forming device; ii) providing a fluid supply device having a second container to provide for supplying a retention agent to ingredients placed within the forming device, the fluid device including an adjustment device for controlling the amount of fluid dispensed; iii) forming a first mixture including ingredients used for animal feed, placing the first mixture in the storage container of the forming device; iv) forming a second mixture including a retention agent comprising alginate, placing the second mixture in the second container; and v) forming a plurality of food articles through the forming device, wherein during forming the second mixture is added to the first mixture to maintain the shape of the resulting formed articles.

It should be appreciated that other features and configurations are contemplated as described and shown herein. Furthermore, without limitation, it is contemplated that the features of the various aspects of the invention may be combined to form new aspects or configurations of the present invention.

DETAILED DESCRIPTION

Figure 1:
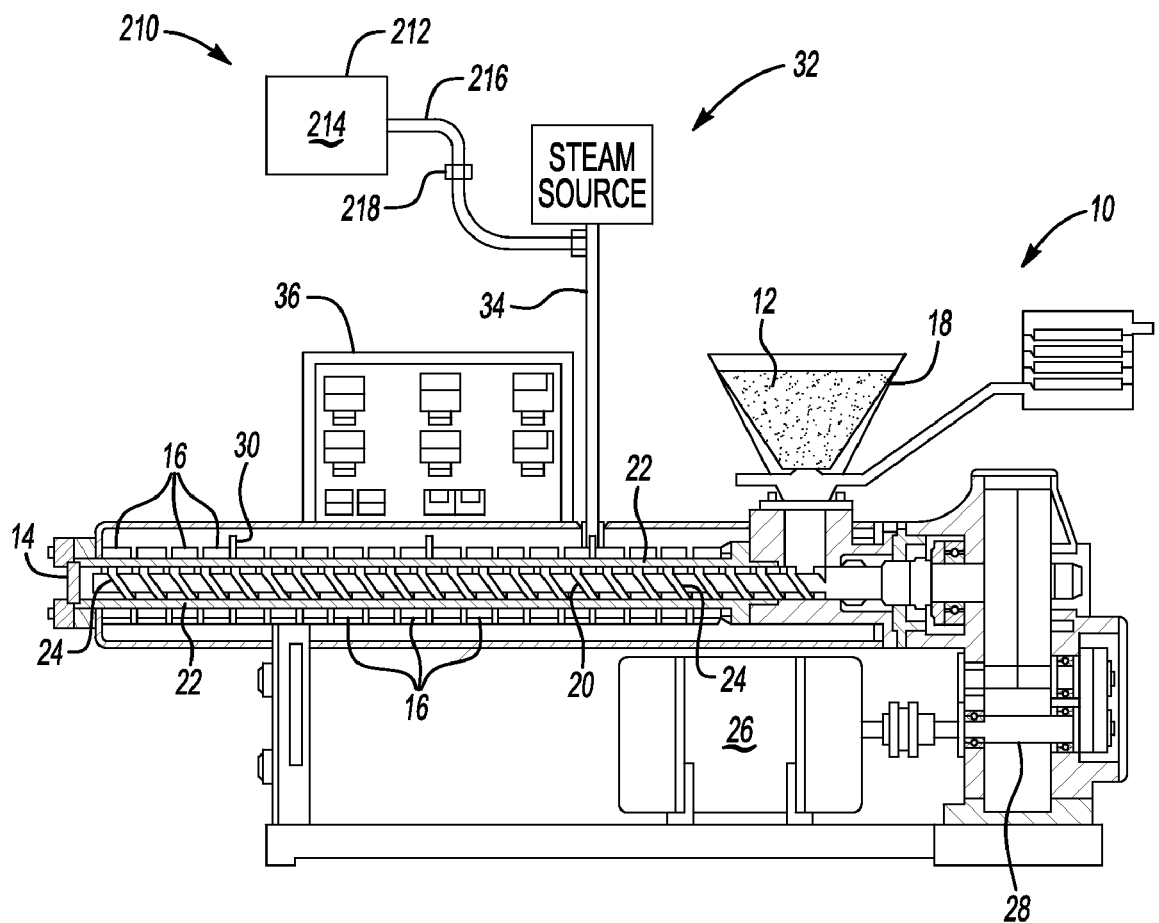
FIG. 1 illustrates one exemplary forming device and method according to the teachings of the present invention.

The present invention provides improved consumable articles (e.g. ingestible, absorbable, or otherwise) and methods and devices for forming the same, through the use of alginate retention agents. The retention agents of the present invention provides a reduction in manufacturing cost and an increase article quality (e.g. resiliency, appearance or otherwise). Furthermore, the use of the retention agents of the present invention may be achieved through the use of new, improved or existing forming devices. The resulting articles have a lower percentage of damaged and/or unusable articles due to breaking, crushing, premature disintegration or otherwise.

As previously mentioned, one particular unique aspect of the present invention is through the use of alginates as a retention agent. It has been discovered that one particularly effective and advantageous alginate comprises sodium alginate. Another particularly advantageous alginate comprises propylene glycol. However, it should be appreciated that many alginates may be suitable for use with the present invention, as described herein. While throughout the description, the retaining agent is described as an alginate and more specifically a sodium alginate, it should be appreciated that other alginates are suitable retention agents and thus should be considered non-limiting.

The present invention also provides forming methods for forming articles through the use of alginates. In one configuration, the method includes forming or modifying mass production forming devices to apply alginate to the ingredients of the article before, during or after forming, or combinations thereof. Through these methods, it contemplate that the present invention provides the ability to monitor and change the characteristics of the articles by modify the application of alginate (e.g. volume, point of application or otherwise). Such characteristics may include durability, hardness, water solubility, or otherwise.

As mentioned above, the retention agent may be added during one or more of the forming steps. In one configuration, the retention agent may be added directly to the ingredients before, during or after mixing thereof. In another configuration, the retention agent may be added during forming of the article such as in a pre-conditioning chamber, adjacent or with a steam applicator, during application of pressure or heat (with a screw of the forming device or otherwise), prior, during or after insertion through a die, combinations thereof, or otherwise. In another configuration, the retention agent may be added in one or more steps after formation of the articles. In still another configuration, the retention agent may be added during one or more of the above mentioned forming steps or otherwise.

While numerous forming devices are contemplated, two particularly useful forming devices comprise extruders or the like and pellet mills or the like. The present invention contemplates providing new or improved forming devices based around extruding or pellet mill forming principals. The present invention also contemplates modification of existing forming devices. In doing so, the present invention includes devices and methods of modifying pre-existing forming devices to include a retention agent applicator. In one example, the modification includes the addition of one or more inputs for introduction of a retention agent during one or more of the forming steps. This may include forming the one or more openings, and hence inputs, through the forming device. This may also include modifying pre-existing inputs, such as a steam or other fluid input, to receive the retention agent. Other configurations are contemplated. In any regards, optionally an automated or manual adjustment device may be provided to regulate the amount of retention agent being applied to the ingredients during forming.

As described above and in more detail below, the features of the present invention provide resulting articles having fewer fines and which are more robust (e.g. more resistant to crumbling and crushing) during handling. However, these articles still remain not only biodegradable but also digestible in certain applications. Also, the method provides stable articles that are resistant to disintegration, or the like, when subjected to moisture, such as high humidity, rain or even placement within water. Accordingly, in one application it is contemplated that the articles may be buoyant.

Through the retaining agents and methods of the present invention it should be appreciated that there exists a broader spectrum of available ingredients and hence available applications. Though many applications of the resulting articles are contemplated, one particularly advantageous application is with the forming of feed or other consumable products for animals. In forming these types of articles, the articles may be consumable to provide nutritional or non-nutritional value and/or may be configured to provide other beneficial results in which the articles are provided, applied, or otherwise given to. By example, these articles may be formed as ingestible feed, which preferably is at least partially digestible, to animals including: humans, livestock (e.g. fish, cattle, poultry (e.g. chickens, turkeys, ducks, geese, or otherwise), pigs, horses, goats, deer, sheep, or otherwise), other domesticated or undomesticated animals (e.g. dogs, cats, ferrets, other fowl, or otherwise), amphibians, reptiles, or otherwise.

In particular, with regards to feed applications, it is anticipated that due to the ability to optimize the formulation of the ingredients for a specific animal (or otherwise), without the necessary use of starches, the conversion rate of the feed to useable animal product is increased resulting in greater value of the animals. In these applications, it is contemplated that the articles may be configured as food, medicine, enzymes, vaccines, growth promoters, combinations thereof, or otherwise. However, in one preferred application, it is contemplated that the resulting articles are configured as food. In this application, it is contemplated that the food articles includes ingredients specifically configured towards the dietary needs of the animal in which it is given.

In another application, the articles may be formed for application to or placement next to other living organism (e.g. plants, microorganisms, or otherwise) for aiding in the growth or development, healing, nutrition or otherwise. In this application, it is contemplated that the resulting articles may comprise fertilizer for general use for a variety of plants or specific use. In yet another application, these articles may be used to prevent disease, protect against harmful insects or animals. Still further, these articles may be for other non-consumable applications.

In still another application, the articles may be formed of combustible ingredients to form a fuel, such as a bio fuel.

Such fuel may be formed of discarded combustible substances such as shredded wood.

In view of the different applications available, it is contemplated that the resulting articles may include numerous combinations of suitable ingredients. Furthermore, in considering the elimination of necessary heat to cause retention of the ingredients, heat sensitive ingredients can now be included as an ingredient of the resulting articles.

For example, it is contemplated that the articles may include one or more ingredients for providing nutritional substance. Such substance may include fats, carbohydrates, protein, dietary fiber, vitamins, minerals, herbs, yeast, other supplements (such as PAYLEAN®, Glycerine, Glycol, or otherwise), combinations thereof, or otherwise. Other examples of suitable ingredients include one or more medicinal substances such as antibiotics, enzymes, anti-viral agents, vaccines, combinations thereof, or otherwise. Still further, other ingredients may assist in growth or development of the consuming recipient, such as one or more steroids, growth hormones, combinations thereof or otherwise. Still further, any combinations of the above referenced ingredients may be included. Other potential ingredients should be appreciated in view of the different applications described herein or otherwise.

Other potential ingredients of the articles include markers (e.g. color dye) to visually identify or enhance characteristics of the feed. Such identification may be particularly useful for identifying articles as being treated or including certain ingredients such as the retention agent or otherwise. Also, such ingredient may be useful in post application or use analysis, wherein the feces of the recipient may be studied to determine digestibility of the ingredients. In one example, the marker may comprise a particularly noticeable color, such as a fluorescent color.

However, the ingredients of the articles may include a color configured to enhance the appearance of the resulting articles, particularly when used as feed. Similarly, flavorings or fragrance may also be added to the articles to entice consumption of the articles by the recipients. Still other optional ingredients include ingredients capable of improving the appearance and/or durability of the resulting article such as surfactants or emulsifiers, gums, combinations thereof or otherwise.

The articles may also include ingredients to assist in the formation, application or distribution of the articles to a given applicant. For example, the articles may include one or more ingredients that provide lubrication for assisting in the formation of the articles or otherwise. In another example, the articles may include one or more elements for improving or providing buoyancy of the article. Alternatively, or in conjunction therewith, the articles may be formed with a predetermined amount of air pockets for achieving buoyancy. In these examples, the retention agent of the present invention may be configured for providing lubrication, buoyancy or both of the articles.

Still further, the articles may also include one or more ingredients for improving the chemical stability of the articles. In one example, the articles may include a calcium sequestration agent (such as sodium hexameta phosphate, or otherwise) for preventing calcium present in water from reacting with the ingredients of the article (such as sodium alginate). For example, the use of calcium sequestration agent may be used to substantially limit or prevent the cross-linking of calcium with any sodium alginate within the article. This cross-linking creates a phase change of the article thereby turning all or a portion or the article water insoluble. Such calcium may comprise part of the ingredients of the article or may be found in the surrounding environment.

Also, it is contemplated that the articles may include ingredients for causing time release of the ingredients. In one example, the time release ingredient comprises one or more layers applied over the ingredients or article that is digestible, biodegradable or otherwise configured to disintegrate and release the enclosed ingredients. In one configuration, it is contemplated that the time release ingredient may also comprise the retention agent of the present invention.

Still further the articles may include ingredients comprising dried distillers grains with solubles (DDGS), crop fodder, fertilizers, switch grass or any other organic or non-organic material that lend themselves to formation into individual articles, which may or may not include a retention agent.

One or more of the ingredients described herein may be selected and mixed together to form a first mixture for forming the articles of the present invention. In view of the available ingredients, it should be appreciated that not all combinations of ingredients may be configured to cohere or remain together during forming. This may be particularly so with starches which, as previously mentioned, requires the application of heat and pressure to cause the ingredients to form together. Advantageously, in at least one configuration, the present invention is configured to maintain the ingredients together after forming of the same. In one aspect, the retaining of the ingredients is achieved without the necessary use of starch. Still further, in one configuration the retention agent comprises an alginate such as sodium alginate, which does not necessarily require the use of heat and pressure to retain the ingredient of the articles together. Of course, in yet another configuration, it is contemplated that the retention agent may be used in conjunction with another retaining agent, including starch or otherwise, to maintain the ingredients together after forming.

As previously mentioned, one unique feature of the present invention is predicated upon the use of non-starch retention agents to maintain the shape of the article (e.g. pellet or otherwise) upon formation. By eliminating or substantially reducing the amount of starch used for retaining the ingredients of the resulting extruded articles, the amount of heat and pressure used to form the articles may be greatly reduced if not substantially eliminated in certain applications. This is because, no longer is it necessary to use such heat and pressure to unravel the particle strands of the starch and retain such unraveled strands together, or otherwise.

In one preferred configuration, the non-starch retention agent comprises or otherwise includes alginic acid (e.g. alginate), which can be found in abundance within the cell walls of algae (such as brown algae or otherwise). Alginate is capable of, under the certain circumstances, retaining the combined ingredients of the article together. This retention is achieved by introducing the alginate to the ingredient of the first mixture prior to, during, or after forming of the articles. While numerous alginates are suitable for use as the retention agent of the present invention, one particularly suitable alginate comprises sodium alginate.

Sodium alginate is a commercially available product often sold by vendors in a powder form. Sodium alginate can be found under trade names such as alginic acid sodium salt, sodium polymannuronate, algin, alginate KMF, algiline, Amoloid®, amnucol, antimigrant C45, cecalgine TBV, Collatex®, Dadrid QH, Dariloid QH, Halltex, Kelacid®, kelco gel LV, Kelcoloid LVF, Kelcosol®, Kelgin®, kelgin LV, Kelgin MDH, Kelgin LDH, kelgum, Kelmar®, kelset, Kelset® keltex, keltone, Keltone® LVCR, Keltone® HVCR, Keltose®, Kelvis®, Lacticol®, manucol, Manucol® LKX, Manugel® LBA, manutex, minus, monason, nouralgine, pectagline, proctin, protanal, protatek, snow algin H, Salmuf, Sahmup, Salmup, Sodium/Calcium alginate, stipine, tagat, Textureze™, tragaya, Welgum®, or otherwise.

In addition to the retention benefits of the alginates, one particular advantageous additional quality is in its ability to act as a lubricant during the forming of the individual articles. The use of alginate as a lubricant can be in addition to its use as a retention agent or it may be used in conjunction with another retention agent (e.g. starch). By providing lubrication during forming, the life span of the forming dies greatly increases due to a reduction in surface friction. Also, the use of lubrication provides the ability for increased pellet throughput by reducing the surface friction and allowing for a decrease in the pressure, which decreases the energy usage. However, in another aspect, the lubrication also allows for the ability to increase pressure of the ingredients during forming as friction forces are reduced. For example, with the reduction of friction forces, increased compression ratio dies can be used, which increases the compression of the ingredients within the forming device, thereby improving pellet retention and quality of the articles. Additionally, this lubrication ability may also assist in the transportation of the articles through feeding systems, such as bulk bins or otherwise.

Another benefit with alginate as a retention agent is the ability to coat the formed articles. Coating the formed articles can provide numerous benefits including, but not limited to, improved article quality, application and longevity. For example, one or more coatings may be formed for providing time release of the ingredients within the article, which may be based upon the layer thickness and/or configuration of the retention agent. In another example, the use of coatings inhibits moisture or water absorption which is known to cause mold growth, decomposition of articles in liquids, mycotoxin contamination, and other negative effects associated with the combination of moisture/water and feed.

Prior to combining or applying the alginate with the ingredients forming the articles, the alginate may be hydrated with the use of water and/or other liquids to form a gel. The hydration of the alginate may be performed in one or more steps to form the retention agent. In one advantageous method, the hydration includes warm water, e.g. water greater than about 100°, greater than about 120°, greater than about 150° or more. The use of warm water decrease the time required for hydration of the alginate and reduces the viscosity thereof. The amount of liquid used to hydrate the alginate may vary depending upon the desired consistency. Preferably, there is a predetermined amount of hydration of the sodium alginate to create a specific retaining configuration. In one configuration, the resulting mixture includes water and between about 0.1% to 10% of sodium alginate, by weight. However, other configurations are available depending on the desired consistency of the resulting mixture.

The retention agent may include between about 0.1% to 10% of alginate, by weight, of the mixture (e.g. alginate and hydrating agent). However, it is also contemplated that the retention agent may include about 0.5% to 5% of alginate, by weight, or even about 0.25% to 3% of alginate, by weight. Other contemplated ranges includes between about 0.1% to 0.25%, 0.25% to 3%, 3 to 4%, by weight, of the retention agent. It should be appreciated that the percent of alginate of the retention agent, and hence the thickness, flowability and viscosity of the second mixture, may depend upon a given form or method of application of the second mixture.

As described herein, the alginate may include one or more additional features or ingredients to form the retention agent of the present invention. For example, while the alginate is contemplated for retaining the ingredients of the articles, alone, it does not foreclose the use of alginate with other retention agents including, but not limited to, traditional retention agents such as starches. Other additional ingredients may include dyes, fragrances, flavors or combinations thereof. Still other potential ingredients may include surfactants or emulsifiers, gums, or combinations thereof. For example, the retention agent may include one or more of the following ingredients: sodium alginate, water, surfactant, growth promoter, mold inhibitor, hormones, steroids, coloring agents, odor agents, taste agents, or otherwise. It should be appreciated that ingredients forming the first mixture may also or alternatively be included with the ingredients forming the retention agent. The ingredients forming the retention agent may be selected and mixed together to form a second mixture. This second mixture is used to act as the retention agent for the ingredients of first mixture. Below is a table of non-limiting examples of the second mixture of the present invention. In this chart the amount of sodium alginate and water mixture is per ton of the first mixture and the surfactant is a percentage of the first mixture.

| Example | Sodium Alginate (lbs/ton) | Water (lbs/ton) | Surfactant (% of mixture) |
|---------|---------------------------|-----------------|---------------------------|
| 1       | 1                         | 40              | 0                         |
| 2       | 1                         | 40              | 0                         |
| 3       | 1                         | 80              | 0                         |
| 4       | 1                         | 40              | 2.5                       |
| 5       | 2                         | 40              | 0                         |
| 6       | 2                         | 40              | 2.5                       |
| 7       | 2                         | 40              | 5.0                       |
| 8       | 2                         | 80              | 0                         |
| 9       | 3.5                       | 40              | 0                         |
| 10      | 4.5                       | 40              | 0                         |
| 11      | 4.5                       | 40              | 2.5                       |

As previously mentioned, the ingredients forming the first mixture, or main staple of the article, may be formed using different forming techniques. Preferably, the forming technique is suitable for forming a plurality of articles in a relatively short period of time. More preferably, the forming technique is also suited for providing the ability of the ingredients to be retained together, by a retention agent of the present invention. The forming technique may be suited for the formation of articles of one or more different size, shapes, densities, or otherwise.

It is contemplated that both low and high pressure forming devices may be used to form the articles of the present invention. For example, suitable high pressure forming devices may include extruding device, pellet mills, high pressure compression molding, or similar devices. In one configuration it is contemplated that the pressure through the die may be greater than about 50 psi, 75 psi, 100 psi, 250 psi, 500 psi, 1000 psi or more. In one configuration it is contemplated that the pressure through the die may be around 85 psi, though certainly others are available. Examples of suitable low pressure forming devices includes vacuum forming molds, casting, rotational molding, low pressure compression molding, or other devices or techniques used in plastic, metal or other forming. Also, it is contemplated that other common forming device may be used with the present invention such as bead forming devices, such as those used for forming plant food, fertilizer, or otherwise.

In a first configuration, the forming technique includes an extruding device. For example, referring to FIG. 1, one suitable extruding device 10 for use with the present invention is shown. The extruding device or extruder is configured for drawing one or more ingredients 12 through the extruder and a die 14 to form a plurality of individual articles. The dies are configured with a plurality of openings such that upon an application of pressure the ingredients are forced through the plurality of openings to form individual articles. The extruder may include one or more heaters 16 for heating the ingredients of the first mixture during extrusion.

Of the available configurations, the extruder may also include a hopper 18 or the like for receiving and storing ingredients of the first mixture or even second mixture used for forming the articles. The hopper may include a mixing device for mixing/blending the ingredients prior to forming. Accordingly, it is contemplated that the individual ingredients of the first mixture, second mixture or both may be placed directly in the hopper and mixed therein. Optionally, the hopper may include one or more applicators for applying a fluid, such as the retaining agent (e.g. second mixture), or otherwise. Other additional features are contemplated such as those typically associated with hoppers.

The extruder may also include a preconditioning chamber for treating the mixed ingredients from the hopper. The preconditioning chamber may be configured to mix and optionally treat the ingredients placed in the hopper. The chamber may also include one or more fluid applicators for applying a fluid to the chamber, such as the retaining agent or otherwise. This fluid may comprise steam for heating, sterilizing or otherwise preparing the ingredient for forming.

The extruder further includes one or more drive mechanism 20 located within the housing 22 (or more specifically one or more cylindrical openings formed in the housing) for moving the ingredients from within the preconditioning chamber or hopper to a die, or otherwise. In one configuration, the one or more drive mechanisms may comprise a screw type drive, such as feed screws, wherein upon rotation of the feed screws the threads 24 thereof rotate within and adjacent the walls forming the cylindrical opening to cause the ingredients to move within the extruder housing. The one or more feed screws may be configured to compress or otherwise apply pressure to the ingredients during movement along the extruder housing. The drive mechanism is activated or powered through the use of a suitable drive motor 26 via linkages 28.

As mentioned above, the extruder may further include one or more heating devices 16 for heating the ingredients forming the articles. The heating devices may be located along the housing forming the opening for the one or more drive mechanism. The heaters may be located external, internal or within the housing. However, preferably, the heaters are configured to transfer a suitable amount of heat to ingredients for the desired purpose (e.g. sterilization, or otherwise).

Optionally, the extruder may further include one or more fluid inputs or ports 30 for providing means for injecting fluid into the extruder during forming of the articles. The fluid inputs may be located along the housing, hopper, die, or otherwise, to assist in sterilization of the ingredients, retention of the ingredients, or otherwise. In one configuration, one or more of the fluid inputs may be used for injecting steam into the extruder. Accordingly, it is contemplated that the extruder includes or is attached to a steam delivery device 32, via a fluid line 34 or otherwise.

In one preferred configuration, the extruder further includes a controller 36 for controlling, monitoring or otherwise regulating one or more of the components of the extruder. For example, it is contemplated that the controller automatically adjusts the amount of retention agent and/or steam being injected or added to the ingredients or articles based upon the mass flow rate of the ingredients or otherwise. The controller may also be manually operated to control function of the extruder based upon the consistency or characteristics of the articles exiting the extruder. It is further contemplated that the controller may control any other the components associated with the extruder 10.

In a second configuration, the forming device technique and device 110 comprises a pellet mill. For example, referring to FIG. 2, one suitable pellet mill for use with the present invention is shown. The pellet mill is configured for drawing in one or more ingredients 112 within the pellet mill and to a die 114 to form individual articles. As with the extruder, it is contemplated that the pellet mill may include a hopper 116 or the like for receiving ingredients for forming the articles. It should be appreciated that the hopper may include all of the features as the hopper described with the extruder, or more, such as mixing device, etc. Furthermore, it should be appreciated that the pellet mill may include one or more of the features described with respect to the extruding device.

The pellet mill also includes one or more preconditioning chamber 118 for treating the ingredients prior to forming. The preconditioning chamber may include one or more applicators for applying a fluid to the ingredients, which may comprise a steam applicator for sterilizing the ingredients, retention agents, both, or otherwise. The preconditioning chamber may also include a mixer for mixing the ingredients together. In the embodiment shown, the mixer is integrated with a drive mechanism for mixing within the chamber and moving the ingredients from one end of the preconditioning chamber to the other.

The pellet mill further includes one or more drive mechanism 120 located within the housing 122 (such as a cylindrical opening formed in the housing) for moving the mixture of ingredients from the preconditioning chamber or hopper to a forming location 124 for individual articles. In one configuration, the one or more drive mechanisms comprise a screw type drive, such as feed screws, wherein upon rotation of the feed screws the threads 126 thereof rotate within and adjacent the walls forming the cylindrical opening to cause the ingredients to move within the housing and to the die 128. The one or more feed screws may also be configured to compress or otherwise apply pressure to the ingredients during movement along the extruder housing. The drive mechanism is activated or powered through the use of one or more suitable drive motor 130.

The pellet mill may further include one or more fluid inputs or port 132 for providing means for injecting fluid into the mill during forming of the articles. The fluid inputs may be located along the housing, hopper, die, or otherwise, for assisting in sterilization of the ingredients, retention of the ingredients, both, or otherwise. In one configuration, one or more of the fluid inputs may be used for injecting steam into the pellet mill. Accordingly, it is contemplated that the pellet mill includes or is otherwise attached to a steam delivery device 134, via a fluid line 136 or otherwise.

Also, optionally as with the extruder, the pellet mill may further include one or more heating devices for heating the ingredients forming the articles. The heating devices may be located along the housing forming the opening for the one or more drive mechanism. The heaters may be located external, internal or within the housing. However, preferably, the heaters are configured to transfer a suitable amount of heat to ingredients for the desired purpose (e.g. sterilization, or otherwise). It should be appreciated that with both the extruder and pellet mill, additional components common thereto may exist. Also, it is contemplated that the pellet mill may also include a controller for controlling, monitoring or otherwise regulating one or more of the components of the pellet mill, as previously described with regards to the extruder.

The present invention also contemplates a retention agent applicator 210 for applying the retention agent, as described herein or otherwise, to the ingredients forming the articles. The applicator may be used with either the extruder or pellet mill as described herein. Of course, it may also be used with other similar type forming devices, or otherwise. The retention agent applicator may comprise an integral component to the forming device or may comprise a separate component. In one particularly advantageous embodiment, the retention agent applicator may be added to a pre-existing extruder, pellet mill, or otherwise to provide a low cost improvement to existing systems.

The retention agent applicator includes a container 212 for holding the second mixture 214 (e.g. retention agent), as described herein or otherwise, which is in fluid communications with the forming device and more preferably the ingredients placed therein (e.g. the first mixture). This fluid communication may be achieved through a tube, pipe, or the like 216, which fluidly connects the container to one or more of the fluid inlets located on the forming device. However, alternatively or in addition therewith, it is contemplated that the retention agent applicator may be in fluid communications with a portion of a steam applicator (e.g. steam source, line, or otherwise). Still further, it is contemplated that the fluid communications may be with another application device, which may be associated with the forming device, for applying the retention agent to the first mixture prior to, during or after forming, or combinations thereof.

The fluid inlet may be connected to or formed on various portions of the forming device for delivery of the retention agent to the ingredients within the forming device. Accordingly, it is contemplated that the fluid inlet may be located at one or more (or even a plurality) of locations at the, ingredient mixer, blender, hopper, preconditioning chamber, forming location, (die, press, and/or otherwise), opening formed through the housing for receiving the drive mechanism, before, after or at the forming location, combinations thereof or otherwise.

In one particularly advantageous application, the fluid inlet may be associated with the input of other fluids entering the forming device. In doing so, the amount of changes necessary to implement the delivery device to a preexisting structure is greatly minimized. Furthermore, as the forming device is already configured to efficiently and effectively apply a fluid, it is expected that the distribution of a retention agent will be fully effectuated.

For example, in one preferred configuration, the fluid inlet is associated with the steam input of the extruder or pellet mill. In doing so, the fluid inlet may be formed with a supply line of the steam, which is configured to apply steam to the ingredients within the ingredient mixer, blender, hopper, preconditioning chamber, opening for the drive mechanism, forming location, or otherwise. Other configurations may be available.

In one preferred configurations, the retention agent applicator further includes an adjustment device 218 for controlling the amount of retention agent being added to the ingredients. The adjustment device may be manual or automatic (e.g. controlled through a controller of the forming device or otherwise) to control the flow rate of the retention agent. The adjustment of the retention agent input may be proportionate to the volume or flow rate of the steam or other fluid entering the forming device. The adjustment may also be based upon flow rate of the ingredients entering or moving through the forming device. In one configuration, the flow rate is adjusted based upon the resulting characteristics of the formed articles, as observed by a user of the device, or otherwise.

In addition to the above configurations, or alternatively, the retention agent may be manually applied, via a handheld or automated spraying device prior to, during, or after the forming of the article. In one embodiment, it is contemplated that a runoff may be provided for recapturing and recovering excess retention agent. In another embodiment, the formed articles may be spread evenly over a table (such as a shaker table), or conveyer and the retention agent is applied thereto.

In view of the different applications, recipients and forming devices, it should be appreciated that the articles may comprise different sizes, shapes, density or otherwise. It is contemplated that the articles may be shaped in different three-dimensional shapes such as spherical, conical, cylindrical, cubical, or otherwise. This may include any shape formed through an extruding process or other mass forming processes. The articles may be generally small (e.g. having a diameter of less than about 1 cm, 0.5 cm, 0.2 cm, 0.1 cm or smaller) or may be larger (e.g. having a diameter greater than about 1 cm, 2 cm, 5 cm or more). In one non-limiting configuration, the article may comprise or otherwise be formed as pellets. The pellets may be formed through a forming process, such as a mass production molding process, as described herein or otherwise. The pellets may be shaped spherically, cylindrically or otherwise.

In the examples of forming device described herein, it is contemplated that the ingredients of the first, second or both mixtures are heated to sterilize the ingredients forming the articles, or otherwise. However, it is also contemplated that the ingredients of the first mixture may not be heated during forming, particularly if one or more of the ingredients within the first mixture is heat sensitive. For example, the ingredients may remain at or about a room temperature, during forming, or even below (e.g. 25° Celsius or below). It is also contemplated that the ingredients maintain a temperature, during extrusion, of about 30° Celsius or below, 35° Celsius or below, 40° Celsius or below, 50° Celsius or below, 70° Celsius or below, or otherwise. Still further, it is contemplated that the temperature of the ingredients during extruding may be as low as about 0° Celsius or several hundred degrees Celsius depending upon the limitation of the ingredients or machine.

Accordingly, it should be appreciated that the temperature of the ingredients during extruding may vary depending upon the application or particular ingredients therein. Also, the temperature may be based upon the nutritional need or desired final product of the article (e.g. texture, form, nutrition or otherwise). In any regards, one unique feature of the present invention is that the temperature of the first and second mixtures during extrusion is not dependent upon a required temperature (or pressure) for activating the retention agent (such as with starches) for bonding the ingredients of the second mixture or article. This is because the use of the retention agent of the present invention (e.g. sodium alginate or otherwise) functions independent of an application of heat. Similarly, the pressure in which the ingredients of the second mixture encounters during forming is also not dependent upon activating the retention agent, such as with starches, for retaining the ingredients of the first mixture.

The present invention includes methods of forming articles, particularly consumable and/or absorbable pellets, using any combinations of the following method features or other features or methods as described herein. In general, the methods include the steps of forming a first mixture comprising one or more ingredients, forming a second mixture including a retention agent, shaping the first mixture and joining the first and second mixture to form the article. In one preferred configuration, the shaping of the first mixture is achieved through rapid forming techniques and may include a retention agent applicator for controlling the flow rate of the second mixture into the first mixture.

The ingredients comprising the first mixture are mixed using typical mixing devices for the mass production of articles, particularly food articles. In one configuration, the mixing device may comprise a device typically used with forming devices such as extruders and pellet mills. Also, it is contemplated that the mixing device may comprise a portion of the forming device, e.g. extruder, pellet mill or otherwise. The ingredients may be mixed prior, during or after placement of the ingredients within the mixing device. After mixture of the ingredients, the first mixture is placed within a forming device or otherwise placed in a position configured for moving into a forming device.

Either before, during or after placement of the first mixture within or proximate to the forming device, a second mixture is formed for retaining the ingredients of the first mixture together. As previously mentioned, in one preferred configuration, the retention agent of the second mixture does not include starch for purposes of retaining the ingredients. In one particularly preferred configuration, the non-starch ingredient comprises sodium alginate. However, as previously mentioned, it should be appreciated that starches may be used in the ingredients of the articles and/or in addition too the sodium alginate for purpose of retention of the ingredients or for other purposes such as dietary needs.

The alginate is hydrated (e.g. water or otherwise) to form a substantially liquid like second mixture, as described herein. The viscosity of the resulting second mixture may vary depending upon the amount of water mixed with the sodium alginate and the dispensing method and requirements (such as volume flow rate or otherwise). Accordingly, the higher the concentration of alginate, by weight, the thicker the resulting second mixture will be. However, in one configuration, the resulting second mixture forms a gelatin mixture, which is configured for fluid movement within a fluid passageway.

The second mixture may be mixed or blended through mechanical means such as through an electrically driven mixer or otherwise. Alternatively, or in conjunction therewith, the second mixture may be mixed manually through a handheld mixing device, automatically or otherwise. Mixture or hydration of the alginate may be performed in the container of the retention agent applicator or in a separate device and subsequently placed in the container. Of course, the second mixture may be formed and/or held in a separated container if the retention agent applicator is used in a hand held dispenser, or otherwise. In any way, preferably the resulting mixture is mixed throughout to form a consistent heterogeneous mixture.

In one optional configuration, the second mixture may be formed during dispensing of the alginate to the first mixture. For example, this may be achieved through the addition of alginate to a fluid entering the forming device. More particularly, in one configuration, this may comprise the addition of alginate to a steam supply line entering the forming device for assisting in forming of articles. In another respect, the second mixture may be heated into a steam and applied to the ingredients of the first mixture.

During mixing, the alginate may be hydrated between about 15-60 minutes or up to 24 hours or several days depending on the contemplated usage. However, the length of time required to hydrate the sodium alginate may be more or less depending on the concentration and characteristics of the sodium alginate or even the dispensing and mixing means of the second mixture. In one configuration, the resulting second mixture is hydrated until substantially the entire mixture becomes a gelatin. It should be appreciated that different time periods and temperatures may be used depending on the type, concentration and characteristics of the alginate.

Upon mixing, the second mixture is placed in a dispensing device, such as the retention agent applicator, or otherwise. With the first and second mixtures prepared and placed in their respective places for dispensing, the forming device begins forming of the individual articles.

In the extruder configuration shown in FIG. 1, the first mixture is placed within the hopper of the extruding device and optionally mixed. The feed screws rotate to draw the first mixture within the opening formed in the housing and through an opening of the extruder housing. As the first mixture is pushed along the opening, the first mixture may be compressed at one or more locations and may also (or alternatively) be heated using the heating devices. Either prior, during or after extruding the first mixture, a retention agent (and preferably an alginate), is injected into or with the first mixture. However, in one preferred configuration, the retention agent (e.g. second mixture) is injected with the ingredients of the first mixture during extrusion and optionally at one or more locations. Still further, the second mixture may be added to any steam entering the extruder for conditioning the same.

When the material reaches the end of the opening formed in the housing, the resulting mixture is forced through a die where the combination of the first and second mixture are molded into the resulting article, which in one preferred embodiment comprises a pellet. Upon exiting the extruder the ingredients of the first mixture are bound together via the second mixture. Optionally, or alternatively, the second mixture including the retention agent may be applied, in one or more applications, to the formed articles upon exiting the extruder.

Based upon the condition of the resulting articles, flow rate of first mixture, steam, or otherwise, the volume flow rate of the second mixture may be adjusted manually or automatically to achieve desired pellet characteristics including reduced fines, improved smoothness or other desired pellet characteristic.

Figure 2:
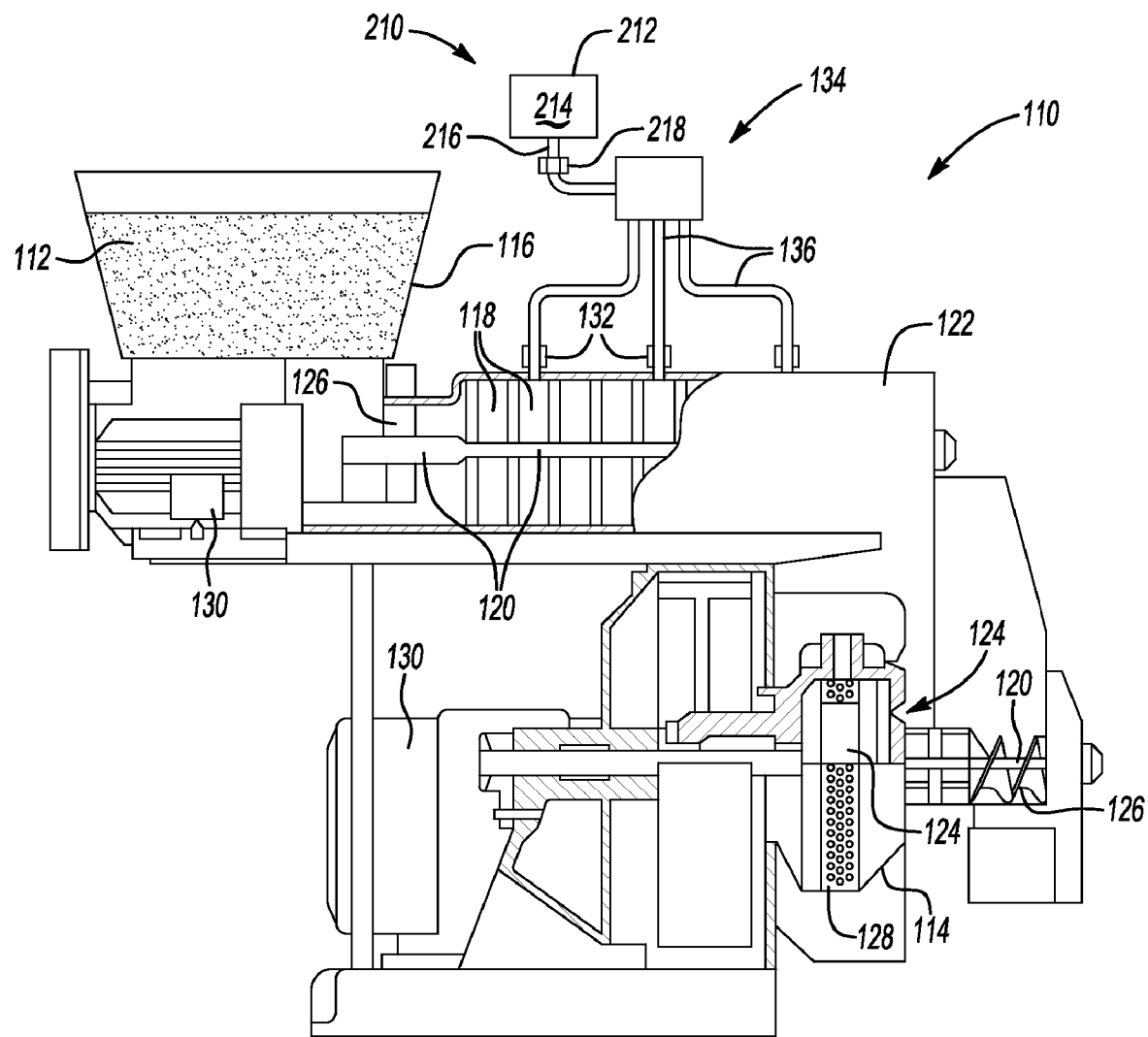
FIG. 2 illustrates another exemplary forming device and method according to the teachings of the present invention.

In another configuration, referring to FIG. 2, the forming device comprises a pellet mill. In this configuration, the first mixture is placed within the hopper of the pellet mill and optionally mixed. The feed screws rotate to draw the first mixture within a preconditioning chamber. In the chamber, steam and optionally the second mixture is added to the first mixture to sterilize the ingredients and cause retention of the ingredients during or after forming of the same. As the first mixture is pushed along the preconditioning chamber, the first mixture is pushed out of the first chamber into the forming location. A second feed screw then moves the combined first and second mixture into or adjacent the die wherein a roller forces the combined first and second mixture through the die to form pellets. Optionally, or alternatively, the second mixture including the retention agent may be applied, in one or more applications, to the formed articles upon exiting the pellet mill.

As with the extruder, based upon the condition of the resulting articles, flow rate of first mixture, steam, or otherwise, the volume flow rate of the second mixture may be adjusted manually or automatically to achieve desired pellet characteristics including reduced fines, improved smoothness or other desired pellet characteristic.

Unless stated otherwise, dimensions and geometries of the various structures depicted herein are not intended to be restrictive of the invention, and other dimensions or geometries are possible. Plural structural components can be provided by a single integrated structure. Alternatively, a single integrated structure might be divided into separate plural components. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention.

The preferred embodiment of the present invention has been disclosed. A person of ordinary skill in the art would realize however, that certain modifications would come within the teachings of this invention. Therefore, the following claims should be studied to determine the true scope and content of the invention.

What is claimed is:

1. A method of forming animal feed, the method consisting the steps of:
    providing a high compression forming device adapted for pelletizing ingredients, the forming device includes a first storage container for receiving and storing a first mixture, a die for shaping the first mixture into pellets and one or more fluid ports for injecting fluid into the first mixture;
    fluidly connecting a retention agent supply device to the forming device, the retention agent supply device includes a second storage container for receiving and storing a second mixture for lubrication and retention of the first mixture;
    fluidly connecting a fluid control device to the retention agent supply device and the one or more fluid ports for metering the amount of second mixture being applied to the first mixture;
    forming the first mixture including one or more ingredients used for animal feed, the ingredients forming the first mixture are disposed in the first storage container of the forming device;
    forming the second mixture, the second mixture includes between about 0.1% to about 10% dry alginate by weight of the second mixture and between about 90% to about 99.9% water by weight of the second mixture, the second mixture is disposed in the second storage container; and
    pelletizing animal feed through compression and movement of the first and second mixture through the forming device to form individual pellets having defined shape, wherein during the entire formation process of the animal feed the ingredients maintain a temperature of at or below about 70° Celsius and the shape and size of the pellets exiting the forming device are maintained by the second mixture and the shape and size of the pellets exiting the forming device are maintained without use of additional retention agents.

2. The method of claim 1, wherein the fluid control device is in communication with a controller for adjustably controlling metering of the second mixture being added to the first mixture.

3. The method of claim 2, wherein the amount of second mixture being added to the first mixture is automatically adjusted based upon the flow rate of the first mixture through the forming device.

4. The method of claim 2, wherein the forming device further includes a steam supply device in communication with the one or more fluid ports for applying steam to the first mixture during forming thereof.

5. The method of claim 4, wherein the amount of second mixture being added to the first mixture is automatically adjusted based upon the flow rate of steam being applied to the first mixture.

6. The method of claim 1, wherein the second mixture further includes a calcium sequestering agent, a surfactant agent or both.

7. The method of claim 1, wherein the alginate comprises propylene glycol alginate.

8. The method of claim 1, wherein the forming device further includes a preconditioning chamber and the second mixture is applied to the first mixture in the preconditioning chamber.

9. The method of claim 1, wherein the high pressure forming device comprises a pellet mill.

10. The method of claim 1, wherein the high pressure forming device comprises an extruder.

11. The method of claim 1, wherein during pelletization the forming device exerts pressure of greater than about 75 psi onto the combined first and second mixture.

12. The method of claim 1, wherein during pelletization the forming device exerts pressure of greater than about 100 psi onto the combined first and second mixture.

13. The method of claim 1, wherein during the entire formation process of the animal feed the ingredients maintain a temperature of at or below about 50° Celsius.

14. The method of claim 1, wherein during the entire formation process of the animal feed the ingredients maintain a temperature and pressure that is below necessary temperature and pressure for binding starches.

15. The method of claim 1, wherein the second mixture includes between about 0.5% to about 5% dry alginate by weight of the second mixture and between about 95% to about 99.5% water by weight of the second mixture.

16. The method of claim 15, wherein the weight ratio of dry alginate to the first mixture is 1/2000 to 4.5/2000.

17. The method of claim 1, wherein the weight ratio of dry alginate to the first mixture is 1/2000 to 4.5/2000.

18. The method of claim 1, wherein the hydrated sodium alginate of the second mixture is substantially the sole retention agent used to maintain the ingredients of the first mixture together.

19. The method of claim 18, wherein the hydrated sodium alginate of the second mixture is substantially the sole lubricating agent used to lubricate the ingredients of the first mixture during pelletization.

* * * * *